United States Patent [19]

Rothman et al.

[11] Patent Number: 5,071,759

[45] Date of Patent: Dec. 10, 1991

[54] HYBRIDOMA CELL LINES AND MONOCLONAL ANTIBODIES TO CLOSTRIDUM DIFFICILE TOXINS A AND B

[75] Inventors: Sara Rothman, Portland, Oreg.; Mary K. Gentry, Bethesda, Md.

[73] Assignee: The United States of America as represented by the Secretary of the Army, Washington, D.C.

[21] Appl. No.: 870,216

[22] Filed: May 30, 1986

[51] Int. Cl.$^5$ ............... C12N 5/20; C12N 15/02; C07K 15/28; C17P 21/08

[52] U.S. Cl. ............... 435/240.27; 530/387; 530/388; 435/70.21; 435/172.2; 436/548

[58] Field of Search ............ 530/387, 388, 825; 435/240.27, 68, 172.2, 842; 436/548; 935/104, 108, 110

[56] References Cited

PUBLICATIONS

Lyerly, D. M. et al. (II), "Characterization of Toxins A and B of *Clostridium difficile* with Monoclonal Antibodies", *Infect. Immun.* 54(1): 70–76, Oct. 1986.
Lyerly, D. M., et al. (III), "Monoclonal and Specific Polyclonal Antibodies for Immunoassay of *Clostridium difficle* Toxin A", *J. Clin. Microbiol.* 21(1): 12–14, Jan. 1985.
Lyerly, D. M. et al. (I), "Monoclonal Antibodies Against Toxins A and B of Clostridium-Difficile", Abstr. Annu. Meet. Am. Soc. Microbiol., Mar. 23–28, 1986, B61, p. 34.
Rolfe, R. et al., "Monoclonal Antibodies Against Clostridium-Difficile Toxins A and B", Abstr. Annu. Meet. Am. Soc. Microbiol., Mar. 23–28, 1986, B62, p. 34.
Rothman, S. W. et al., "Differential Cytotoxic Effects of Toxins A and B Isolated from *Clostridium difficile*", *Infect. Immun.* 46(2): 324–331, Nov. 1984.

*Primary Examiner*—Esther L. Kepplinger
*Assistant Examiner*—Paula Hutzell
*Attorney, Agent, or Firm*—Werten F. W. Bellamy

[57] ABSTRACT

Monoclonal antibodies produced by a family of murine hybrid cell lines are cross-reactive with both toxin A and toxin B of *Clostridium difficile*. The monoclonal antibodies are useful in an immunoassay for toxin A and toxin B of *C. difficile*, a casual agent of antibiotic-associated pseudomembranous colitis in humans and animals.

17 Claims, 6 Drawing Sheets

ASCITIC FLUID DILUTION (LOG$_{10}$)

HYBRIDOMA CELL LINES AND MONOCLONAL ANTIBODIES TO CLOSTRIDUM DIFFICILE TOXINS A AND B

BACKGROUND OF THE INVENTION

*Clostridium difficile*, the etiological agent of pseudomembranous colitis in humans and animals, produces two toxins, designated toxin A and toxin B, that are cytotoxic for tissue-cultured mammalian cells. Toxin B is approximately 1,000-fold more cytotoxic than toxin A per mg of protein, however. In addition to its cytotoxicity, toxin A also possesses enterotoxin activity and causes a fluid response when injected into ligated rabbit intestinal loops.

While toxin A and toxin B can be quantitated by their activity against tissue culture cells, the greater activity against tissue culture cells of toxin B interferes with the detection of toxin A by this assay. As a consequence, the two toxins have to be separated before the assay to determine the cytotoxic titer of toxin A. The different activities of toxins A and B in the rabbit intestinal loop and suckling mouse assays indicate that these assays might be useful in detecting toxin A; however, both assays are tedious and not very sensitive. An enzyme-linked immunosorbent assay (ELISA) using affinity-purified antibody against toxin A has been developed which is said to be specific for toxin A and does not require an initial separation of toxins A and B. The sensitivity of the disclosed ELISA procedure for tissue culture-positive fecal specimens is only 59%, but more sensitive enzyme immunoassays for toxin A and toxin B, respectively, have been reported. Laughon et al, *J. Infectious Diseases* 149: 781–88 (1984). Aronsson et al also discloses ELISA's for either toxin A or toxin B. "Enzyme immunoassay for detection of Clostridium difficile toxins A and B in patients with antibiotic-associated diarrhoea and colitis," *Eur. J. Clin. Microbiol.* 4: 102–07 (1985).

Lyerly et al have compared monoclonal antibody, affinity-purified polyclonal antibody, and monospecific antiserum against toxin A by counterimmunoelectrophoresis, latex agglutination, and ELISA. *J. Clin. Microbiol.* 21: 12–14 (1985). But a single monoclonal antibody-based assay sensitive to both toxin A and toxin B, without the above-mentioned interference effect, has apparently not been reported. Indeed, the absence of reported polyclonal antibody cross-reactivity between the toxins suggested that a cross-reactive monoclonal antibody might not exist.

SUMMARY OF THE INVENTION

It is therefore an object of the present invention to provide fused somatic cell lines that produce monoclonal antibodies displaying immunological cross-reactivity between toxin A and toxin B.

It is another object of the present invention to provide monoclonal antibodies that recognize toxin A and toxin B of *C. difficile*.

It is yet another object of the present invention to provide a single immunoassay that can detect the presence in a sample of toxin A, toxin B, or both toxins together.

In accomplishing the foregoing objects, there have been provided, in accordance with one aspect of the present invention, murine monoclonal antibodies that are cross-reactive with both toxin A and toxin B of *Clostridium difficile*. In a preferred embodiment, the monoclonal antibodies of the present invention have an A/B reactivity ratio, as measured by radioimmunoassay, of between about 0.5 and about 6.9. In another preferred embodiment, the monoclonal antibodies of the present invention are produced by continuous hybrid cell lines which are the product of a process comprising the step of fusing (i) mouse spleen cells from a mouse immunized with a mixture comprising cytotoxically neutralized toxin A and toxin B and (ii) mouse myeloma cells.

In accordance with another aspect of the present invention, there have been provided continuous hybrid cell lines that produce murine monoclonal antibodies which are cross-reactive with both toxin A and toxin B of *Clostridium difficile*.

In accordance with yet another aspect of the present invention, there has been provided an immunoassay for the presence of *Clostridium difficile* which utilizes murine monoclonal antibodies that are cross-reactive with *C. difficile* toxins A and B.

Other objects, features, and advantages of the present invention will become apparent from the following detailed description. It should be understood, however, that the detailed description and specific examples, while indicating preferred embodiments of the invention, are given by way of illustration only since various changes and modifications within the spirit and scope of the invention will become apparent to those skilled in the art from this detailed description.

DETAILED DESCRIPTION OF THE PREFERRED EMBODIMENTS

Figure 1A:
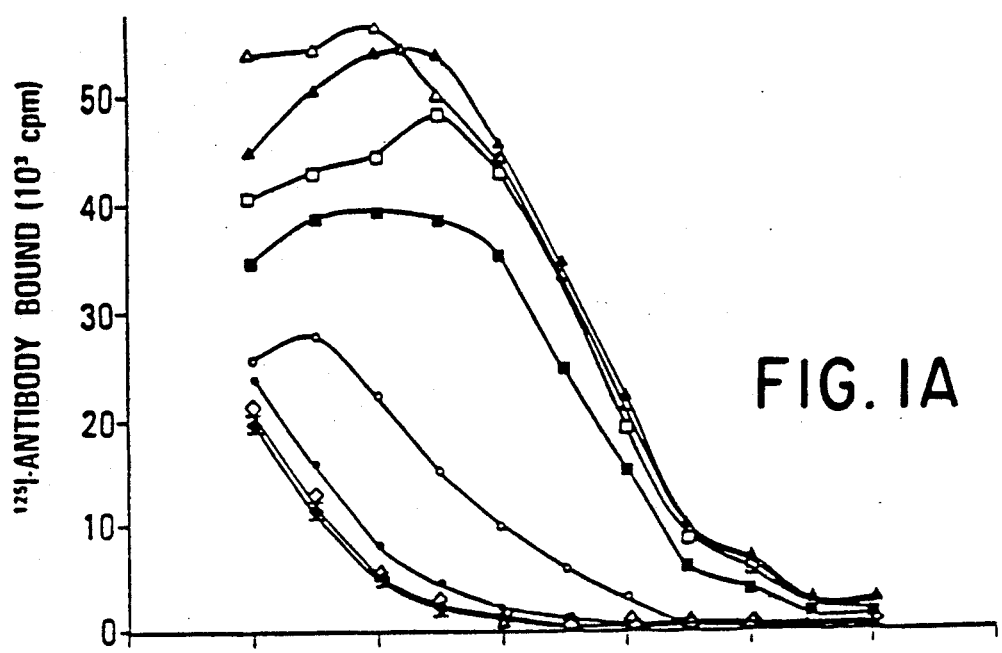
FIGS. 1A and 1B are graphs showing the amount of mouse polyclonal antibody that is bound by varying concentrations of *C. difficile* toxin A and toxin B, respectively.

The present invention involves the production of monoclonal antibodies against the purified proteins that are *C. difficile* toxins A and B, respectively. Purified toxins can be prepared, for example, by the method of Rothman et al, "Differential cytotoxic effects of toxins A and B isolated from Clostridium difficile," *Infect. Immun.* 46: 324–31 (1984) ("Rothman, 1984"), the contents of which are hereby incorporated by reference. In particular, toxins A and B can be purified from dialyzed filtrates of a cultured *C. difficile* strain by hydrophobic interaction chromatography (HIC), followed by ion-exchange chromatography and concentration, e.g., either by dialysis or by ultrafiltration. (The term "dialyzed filtrate" is used herein to refer to the crude filtrate obtained when a *C. difficile* strain is grown anaerobically in a dialysis bag suspended in a suitable nutrient medium, such as brain heart infusion broth. See Rothman and Brown, "Inhibition of membrane functions in intact HeLa cells by *Clostridium difficile* cytotoxic culture filtrates," *Curr. Microbiol.* 6: 221 (1981). the contents of which are hereby incorporated by reference.) Typically, the *C. difficile* strain employed as the source for toxin A and toxin B immunogens can be grown in 100 ml phosphate-buffered saline in a dialysis bag suspended in 3 liters of Difco brain-heart infusion broth. Before the culture is inoculated, the flask is gassed with $N_2$, $H_2$ and $CO_2$, to replace dissolved $O_2$, and sealed to maintain anaerobiosis. After incubation at 35° C. for 5 days to allow maximum expression of toxin in the medium, cells can be sedimented by centrifugation (twice for 10 minutes at 48,000×g has proved suitable), and the supernatant fluids then sterilized by filtration, e.g., through a 0.45-μm Millipore membrane, to obtain the dialyzed filtrate.

Generally, substances are separated via HIC on the basis of differing strengths of their hydrophobic interactions with an uncharged bed material which contains hydrophobic groups. The HIC fractionation of the *C. difficile* dialyzed filtrate initially entails raising the ionic strength of the filtrate, e.g., by the addition of a readily ionized salt like ammonium sulfate, in order to render highly hydrophilic the solvent environment for proteins in the dialyzed filtrate. The filtrate is then passed over a chromatography column which provides a distinctly nonpolar moiety, such as the phenyl group available in a matrix comprised of a phenyl-substituted cross-linked agarose gel filtration medium (PHENYL-SEPHAROSE CL-4B, manufactured by Pharmacia Fine Chemicals, Inc., Piscataway, N.J.). Relatively hydrophobic proteins in the dialyzed filtrate, including both toxins A and B, are retained by such a column. Moreover, the *C. difficile* toxins can be eluted from the column, essentially together, by imposing a linear gradient of increasing hydrophobicity, for example, a buffered ethylene glycol gradient. Thus, elution is effected by decreasing the strength of the hydrophobic interaction between the nonpolar moiety and the surface-exposed hydrophobic areas of the toxins.

The desired eluted fraction, identified by its cytotoxicity as the one containing the *C. difficile* toxins, is then subjected to ion-exchange chromatography, e.g., employing a bead-formed, agarose gel anion exchanger medium. A weak anion exchanger like DEAE-SEPHAROSE CL-6B (manufactured by Pharmacia Fine Chemicals, Inc., Piscataway, N.J.); which preferentially binds biopolymers of greater than 10,000 molecular weight, can be used in this context.

Both toxin A and toxin B are lethal to animals when injected in amounts sufficient to elicit an immune response. To obtain primed mouse lymphocyte cells for subsequent fusion with an immortalizing mouse myeloma cell line, mice must therefore be injected with toxoids prepared from purified toxin A and toxin B, respectively. By definition, a "toxoid" is a toxin of a pathogenic organism treated so as to destroy its toxicity but leave it capable of inducing the formation of antibodies on injection. In accordance with the present invention, it is preferred that toxoids of toxins A and B be produced by incubating each toxin with glutaraldehyde, which is believed to act as a cross-linking agent joining two or more toxin molecules in a toxoid complex. It is particularly preferred that the respective toxoids of the two toxins, however prepared, should be pooled to provide an immunogenic mixture for injection.

EXAMPLE 1

Preparation of Purified *C. difficile* Toxins

Toxins A and B were purified from dialyzed filtrates of *C. difficile* strain VPI10463 (made publically available by Dr. N. M. Sullivan, Dept. Anaerobic Microbiology, Virginia Polytechnic Institute and State University, Blacksburg, Va. 24061); any *C. difficile* strain that produces both toxin A and toxin B can be used, however. In subsequent purification steps, Tris buffers were used, and are referred to hereinafter as follows: Buffer "20T8" consisted of 0.020M Tris hydrochloride (pH 8.0). With 80 and 100 mM NaCl, this buffer was designated "20T8/80" and "20T8/100", respectively.

The initial hydrophobic interaction chromatography step (see Table 1) was performed at 25° C. in an 8- by 7-cm column at a flow rate of 6.3 ml/min.

TABLE 1

| | Purification of C. difficile toxins from dialyzed filtrates | | | | | |
|---|---|---|---|---|---|---|
| Prepn | Vol (ml) | Cytotoxicity (MCD/ml) | Protein (mg/ml) | Sp act (MCD/mg) | Purification (fold) | Recovery[a] (%) |
| Dialyzed filtrates | 2,600 | $1 \times 10^{7a}$ | 1.1 | $9 \times 10^6$ | 1 | 100 |
| Phenyl-Sepharose CL-4B | 830 | $6 \times 10^{7a}$ | 0.9 | $7 \times 10^7$ | 8 | 100 |
| DEAE-Sepharose CL-6B | | | | | | |
| Toxin A | 30 | $5 \times 10^5$ | 3.9 | $1 \times 10^5$ | 1 | |
| Toxin B | 120 | $1 \times 10^8$ | 0.31 | $3 \times 10^8$ | 33 | 46 |
| Concentration | | | | | | |
| Toxin A, PEG 20 | 8.5 | $4 \times 10^6$ | 25 | $2 \times 10^5$ | $2^b$ | |
| Toxin B, Amicon XM-100A | 6.0 | $2 \times 10^9$ | 5.6 | $4 \times 10^8$ | 44 | 46 |

[a] Values for toxin B only.
[b] Value for toxin A only after DEAE treatment.

Ultrapure grade ammonium sulfate (manufactured by Schwartz/Mann, Orangeburg, N.Y.) was added to the filtrate to a concentration preferably just below that at which salting out of protein occurs. (Typically, no precipitate formed when the salt concentration was increased to about 15% saturation.) The sample (2,600 ml) was then applied to a PHENYL-SEPHAROSE column (PHENYL-SEPHAROSE CL-4B, manufactured by Pharmacia Fine Chemicals, Inc., Piscataway, N.J.) which had been equilibrated with starting buffer (20T8/100 buffer, 15% saturated with ammonium sulfate). The column was thereafter eluted with starting buffer. No toxin was detected in the initial 1,800-ml eluant of nonbinding protein. Elution with a linear gradient of 0 to 50% ethylene glycol in 20T8/100 buffer yielded a single absorbance peak, with cytotoxic activity being highest at a conductivity of about 20 mmho. The toxin-containing fractions were pooled and dialyzed for 36 h at 4° C. with three changes of 20T8/80 buffer. Total toxin activity was enriched eightfold with 100% recovery. All further steps were at 4° C.

Ion-exchange chromatography was performed in a 6.5- by 7-cm column at a flow rate of 3.2 ml/min. The toxin preparation (830 ml) was applied to a DEAE-SEPHAROSE CL-6B column equilibrated with 20T8/80 buffer, followed by elution with the same buffer. Elution with a linear salt gradient from 80 to 500 mM NaCl in 20T8 buffer yielded two cytotoxic bands, designated toxins A and B in accordance with the nomenclature used by Sullivan et al, "Purification and characterization of toxins A and B of Clostridium difficile," *Infect. Immun.* 35: 1032 (1982). Toxin A eluted with the large absorbance peak at 12 mmho. Toxin B was detected at a conductivity of 25 mmho where there was little detectable absorbance. Pools of toxins A and B were concentrated by ultrafiltration (XM-100A membrane, manufactured by Amicon Corp., Danvers, Mass.) or by dialysis against polyethylene glycol (20,000 daltons in dialysis tubing which excluded 12,000 daltons). Purified toxins were stored at 4° C.

EXAMPLE 2

Preparation and Injection of Toxoids

Purified toxin A (19 μg/ml) was incubated in 0.08% glutaraldehyde, and purified toxin B (6.4 μg/ml) in 0.1% glutaraldehyde, in 20 mM Tris HCL, 100 mM NaCl (pH 8) at 37° C. for 2 hours. Lysine at twofold molar excess over glutaraldehyde was added (37° C., 15 minutes) to stop the reactions. After dialysis, the toxoid solutions (toxin A, 13 μg/ml; toxin B, 4.3 μg/ml) were stored at 4° C. To prime lymphocytes, BALB/c mice (Jackson Laboratories, Bar Harbor, Me.) were thereafter injected intramuscularly with a mixture of toxoid A and toxoid B, 0.6 μg each in 0.2 ml. Freund's complete adjuvant, 0.1 ml, was also injected intraperitoneally. On day 146 after injection, the mice received booster shots intravenously with the same amount of the mixed toxoids.

EXAMPLE 3

Preparation of Activated Spleen-cell Dispersion

On day 149, the mice injected with the toxoid mixture as described above were sacrificed and their spleens removed. In accordance with Gentry et al, "Identification of distinct antigenic determinants on dengue-2 virus using monoclonal antibodies," *Am. J. Trop. Med. Hyg.* 31(3): 548–555, the contents of which are hereby incorporated by reference, the mouse spleens were teased through a 60-mesh screen, and the fragments rinsed with Dulbecco's minimum essential medium with high glucose (DMEM) containing 20% fetal bovine serum (FBS). The resulting cell suspension was allowed to settle for 5 minutes and the supernatant was removed and centrifuged at 1,000 rpm for 5 minutes at room temperature in an IEC-2R centrifuge to collect the spleen cells. The cells were resuspended in 5 ml of 0.17M $NH_4Cl$ to lyse the red cells, diluted in DMEM with 20% FBS, and the spleen cells were pelleted. The concentration of live cells was determined by trypan blue exclusion.

Preferably on the same day the mouse spleen cells are prepared as described above, cell fusion with a murine myeloma cell preparation can be effected, for example, following the technique of Kennett et al, "Hybrid plasmacytoma production: Fusions with adult spleen cells, monoclonal spleen cells, monoclonal spleen fragments, neonatal spleen cells and human spleen cells," *Curr. Top. Microbiol. Immunol.* 81: 77–91 (1978), the contents of which are hereby incorporated by reference. The choice of fusion technique is not crucial; protocols for hybridization which use polyethylene glycol are preferred. See Note, "Protocols for hybridization with PEG," *Art Sci. Tissue Culture* 4(1): 4 (1985). Selection of an immortalizing myeloma line for fusion purposes is also not critical, although a line that does not itself secrete antibody (a "non-secretor" line) is preferred. The murine myeloma cell line P3×63 Ag8.653 (ATCC CRL 1575), developed by Kearney et al, "A new mouse myeloma cell line that has lost immunoglobulin expression but permits the construction of antibody-secreting hybrid cell lines," *J. Immunol.* 123(4): 1548–50 (1979), is suitable for use in producing a fusion product in accordance with the present invention.

EXAMPLE 4

Illustrative Cell Fusion Procedure

Thus, following Kennett et al, myeloma cells of the P3×63 Ag8 line were maintained in growth medium with the addition of 5 μg/ml 8-azaguanine. The day before fusion, the myeloma cells were subcultured by diluting 1:2 in fresh medium. Approximately $10^7$ myeloma cells were then mixed with $1.5 \times 10^8$ spleen cells, rinsed free of serum, and resuspended in 0.2 ml of 30% polyethylene glycol 1000 (J. T. Baker Chemical Co., Phillipsburg, N.J.) for a total of 8 minutes, during which time they were centrifuged for 6 minutes at room temperature at 1,000 rpm. At 8 minutes, the polyethylene glycol was diluted by the addition of 5 ml DMEM, then with an additional 5 ml of DMEM with 20% FBS. After centrifugation, the cell mixture was suspended in 30 ml of the "HY medium" of Kennett et al and dispensed into 96-well plates in 50 μl aliquots. After 24 hours 100 μl of HY medium with $6 \times 10^{-7}$M aminopterin were added to each well. Thereafter, aminopterin concentration was maintained at $4 \times 10^{-7}$M.

An immunoassay was developed for use in screening hybrid cell lines for antibody production in accordance with the present invention. Generally, the steps involved in establishing an effective assay include (1) preparing polyclonal mouse antibodies against *C. difficile* toxins and (2) measuring the binding of antibody by the toxin. To effect step (1), polyclonal hyperimmune mouse ascitic fluid (HMAF) was prepared, following Brandt et al, "Production and characterization of arbovirus antibody in mouse ascitic fluid," *Am. J. Trop. Med. Hyg.* 16: 339–47 (1967), by immunizing mice with a crude cytotoxic culture filtrate of *C. difficile* which had been neutralized by the addition of excess rabbit antiserum (see Rothman, 1984). Outbred WRM: (ICR) BR mice (Charles River Laboratories, Wilmington, Mass.) were injected with the antigen-antibody mixture on days 1 and 3: intramuscularly (0.1 ml), subcutaneously and intraperitoneally (0.2 ml each). On day 3, Freund's complete adjuvant (0.1 ml) was separately injected intraperitoneally. A separate injection of freshly harvested sarcoma 180 cells (0.3 ml) was given on day 30 to induce ascites. The fluids, which contained polyclonal antibodies to the *C. difficile* toxins, were harvested on day 45 by gravity flow through a 16-gauge hypodermic needle.

To determine optimum binding conditions in a solid-phase radioimmunoassay (RIA), RIA plates were prepared by drying dilutions of *C. difficile* toxin A and toxin B purified in the manner described above, in 96-well flexible assay plates (manufactured by Falcon Labware, Oxnard, Calif.). Dilutions of primary antibody, i.e., the polyclonal antibody mixture contained in the HMAF, were added and incubated 4–18 hours at room temperature. To reveal the extent of binding between the primary antibody and the plated antigen, a second detecting antibody broadly reactive to mouse antibody is used to attach a "label," such as a radionuclide in the case of an RIA, a fluorescent molecule in the case of a fluorescent antibody assay, or enzymes such as alkaline phosphatase or horseradish peroxidase in the case of an enzyme linked immunosorbent assay (ELISA), to the antigen-primary antibody complexes. In the present example, the detecting antibody was affinity-purified goat antiserum to mouse IgG, IgA and IgM (obtained from Kirkegaard & Perry Laboratories, Gaithersburg, Md.) which had been labeled with $^{125}$I to approximately $2.5 \times 10^5$ cpm/25 μl via the "chloramine T" method described by Greenwood et al, "The preparation of $^{131}$I-labeled human growth hormone of high specific radioactivity," *Biochem.* 89: 114–23 (1963), the contents of which are hereby incorporated by reference. The diluent used was Dulbecco's phosphate buffered saline with 0.5% sodium azide; blocking and rinsing were diluent to which fetal bovine serum (20%) had been added.

Antibody-secreting cell lines produced, in accordance with the present invention, by fusion of toxoid-activated mouse lymphocytes and mouse myeloma cells were identified by means of the above-identified RIA developed using HMAF. More specifically, the above-described RIA was first employed to establish effective conditions for detecting polyclonal antibodies in mouse hyperimmune ascitic fluids, particularly the range of toxin concentrations over which the binding antibody could be readily observed. Results of binding of this polyclonal antiserum to toxin A and toxin B are shown in FIG. 1. In FIG. 1A, the concentrations for toxin A (in nanograms (ng) per well) are: Δ, 450; ▲, 230; □, 110; ■, 56; ○, 28; ●, 14; ◇, 7.0; ◆, 3.5. In FIG. 1B, the concentrations for toxin B (ng per well) are: Δ, 180; ▲, 90; □, 45; ■, 23; ○, 11; ●, 5.6; ◇, 2.8; ◆, 1.4. Each data point is the mean of duplicate determinations. Toxin A and toxin B were observed to bind mouse polyclonal antibodies over a range of toxin concentrations. Toxin A readily bound antibody at a concentration of 56 ng/well, toxin B at 45 ng/well.

Thereafter, the RIA was used to screen primed lymphocyte/myeloma fusion products; the highest toxin concentrations tested (see FIG. 1) were used in the assay so that low antibody concentrations could be detected. Thus, about 450 ng of purified toxin A or about 180 ng of purified toxin B were added per well to the assay plates prepared as previously described to detect even low levels of antibody present in the supernatant fluids of desired fused-cell cultures. In this way, 124 hybrid cell lines were identified, all producing antibodies that bound both toxin A and toxin B. Twenty hybrids, selected to represent a range of cross-reactivity values, were cloned twice and further characterized, as described below. One cell line of the select group proved somewhat unstable and was ultimately discarded.

To ascertain the isotype of the antibodies produced by those cell lines identified by the RIA screening, heavy and light chain classes of the monoclonal antibodies were determined by radioimmunoassay. *Clostridium difficile* toxin A or goat anti-mouse antibodies (450 ng or 31 ng/well, respectively) were dried onto assay plates. Undiluted culture supernatant fluids (25 μl) from a hybrid cell line were allowed to react overnight and were then removed by rinsing. Thereafter, 2.5 μg (25 μl) of rabbit antisera to mouse immunoglobulin isotype subclasses (produced by Litton Bionetics, Charleston, S.C.) were added. After 2 to 4 hours, anti-isotype antibodies were removed by rinsing, and binding was detected with 25 μl goat antiserum to rabbit immunoglobulins, G, A, and M (produced by Calbiochem, San Diego, Calif.). Before use in this assay, the goat anti-mouse antiserum had been affinity-purified on glutaraldehyde-treated rabbit serum, following Avrameas and Ternynck, "The cross-linking of proteins with glutaraldehyde and its use for the preparation of immunoadsorbents," *Immunochem.* 6: 53–66 (1969), and labeled with $^{125}I$ to approximately $2.5\times10^5$ cpm/25 μl using the chloramine T method of Greenwood et al, cited above.

The antibodies produced by all of the 124 screened fused-cell lines mentioned above were, with two exceptions, of the IgM isotype. In two cases, the isotype appeared to be mixed IgM and $IgG_{2a}$ or $IgG_1$. All light chains of the antibodies were kappa, save in one instance of mixed kappa and lambda and two other instances of lambda. All the antibodies produced by the nineteen cloned hybrids were of the IgM isotype.

For the nineteen cloned hybrids selected for further characterization, the binding of produced monoclonal antibodies to *C. difficile* toxin A and toxin B was determined in a solid-phase radioimmunoassay in which equal amounts of toxin A or toxin B (380 ng) were added per well. The antibody preparations were the undiluted tissue culture fluids of the cloned hybrids, respectively. The results of the binding assay are shown in Table 2. Cultures of each of the nineteen hybrids were deposited with the American Type Culture Collection (Rockville, Md.) under accession numbers also shown in Table 2. The date of deposit for the hybridomas listed in TABLE 2 are as follows:

(1) For ATCC Numbers HB9028, HB9029, HB9030, HB9031, HB9032 and HB9033 the deposit date was Mar. 11, 1986;

(2) For ATCC Numbers HB9055, HB9056, HB9057, HB9058, HB9059, HB9060, HB9061, HB9062, HB9063, HB9064, HB9065, HB9066 and HB9067 the deposit date was Apr. 1, 1986.

From the binding assay, it was observed that all of the monoclonal antibodies secreted by the 19 hybrid lines produced in accordance with the present invention reacted with both toxins. More specifically, the monoclonal antibodies of the present invention can be divided into at least two groups: those that bound more strongly to toxin A than to toxin B, and those that bound about equally to each. For the 19 tested hybrids, the ratio of antibody bound to toxin A versus to toxin B (see "ratio A/B" in Table 2) ranged between about 0.5 and about 6.9 for the undiluted tissue culture supernatant fluids. (Background binding ranged from 115 to 270 cpm.) This binding assay was also performed to titrate the binding of a series of concentrations of the 19 monoclonal antibodies. The results of this titration are shown in FIGS. 2A–2D, which demonstrate reaction of some of the antibodies with toxin A (open circles) and toxin B (filled circles) over the whole range of concentrations from undiluted through the $2^{-11}$ dilution.

TABLE 2

Radioimmunoassays of Monoclonal Antibodies vs. C. difficile Toxins

| Hybridoma line | ATCC Deposit Accession No. | RIA (mean cpm) ToxA | RIA (mean cpm) ToxB | Ratio A (cpm)/ B (cpm) |
|---|---|---|---|---|
| T3-1C9  | HB9033 | 10393 | 3211  | 3.2 |
| T3-1C12 | HB9030 | 14861 | 13008 | 1.1 |
| T3-1D8  | HB9032 | 12095 | 8192  | 1.5 |
| T3-1E5  | HB9029 | 22497 | 21126 | 1.1 |
| T3-1E7  | HB9055 | 6315  | 13396 | 0.5 |
| T3-1E10 | HB9060 | 3878  | 2561  | 1.5 |
| T3-2A9  | HB9028 | 21167 | 17124 | 1.2 |
| T3-2B1  | HB9057 | 8037  | 1168  | 6.9 |
| T3-2D2  | HB9061 | 2495  | 1390  | 1.8 |
| T3-2G4  | HB9058 | 794   | 893   | 0.9 |
| T3-2H5  | HB9056 | 25029 | 19140 | 1.3 |
| T3-2H6  | HB9062 | 14832 | 16931 | 0.9 |
| T3-3F11 | HB9059 | 6212  | 2864  | 2.2 |
| T3-3H1  | HB9064 | 18431 | 18126 | 1.0 |
| T3-4A7  | HB9063 | 19206 | 16139 | 1.2 |
| T3-4C11 | HB9031 | 18612 | 21214 | 0.9 |
| T3-8B8  | HB9066 | 2745  | 3184  | 0.9 |
| T3-8F5  | HB9067 | 14662 | 6166  | 2.4 |
| T3-9E7  | HB9065 | 12269 | 3670  | 3.3 |

Recognition of both toxins A and B by the monoclonal antibodies of the present invention was confirmed by immunoblotting using a Western blot technique like that described by Burnette, "'Western blotting': Electrophoretic transfer of proteins from sodium dodecyl sulfate-polyacrylamide gels to unmodified nitro cellulose and radiographic detection with antibody and radioiodinated Protein A," *Analyt. Biochem.* 112: 195–203 (1981), the contents of which are hereby incorporated by reference. Electrophoresis was first carried out in 5.5% slab gels by the method of Davis, "Disc electrophoresis, II. Method and application to human serum proteins," *Ann. N.Y. Acad. Sci.* 121: 404–27 (1964). Purified *C. difficile* toxin A (98 μg) and toxin B (180 μg), prepared in accordance with Rothman, 1984, were mixed and added in a volume of 1.7 ml to a single, long well formed with a blank comb. After electrophoresis, an edge section was cut off and stained with Coomassie blue dye. Proteins from the major portion of the gel were transferred electrophoretically to nitrocellulose and processed as previously described by Brown et al, "Purification and biological characterization of Shiga toxin from *Shigella dysenteriae* 1.," *Infect. Immun.* 36: 996–1005 (1982), the contents of which are hereby incorporated by reference, with the following modifications. After protein transfer, the nitrocellulose was cut into strips to allow separate processing. The nitrocellulose strips were incubated sequentially in buffer containing bovine serum albumin (filler), filler and monoclonal antibody (1:20 dilution of tissue culture supernatant fluids), filler and affinity-purified rabbit antiserum to mouse immunoglobulins (14 μg/ml), and filler and $^{125}$I-labeled protein A ($5 \times 10^5$ cpm/ml), respectively. Addition of affinity-purified rabbit antiserum amplified the reaction of the antigens with the monoclonal antibodies. To reduce background, rabbit antiserum raised against mouse immunoglobulins G, A and M (Calbiochem, La Jolla, Calif.) was purified by affinity chromatography using cross-linked normal mouse serum as the immunoadsorbent.

Figure 3:
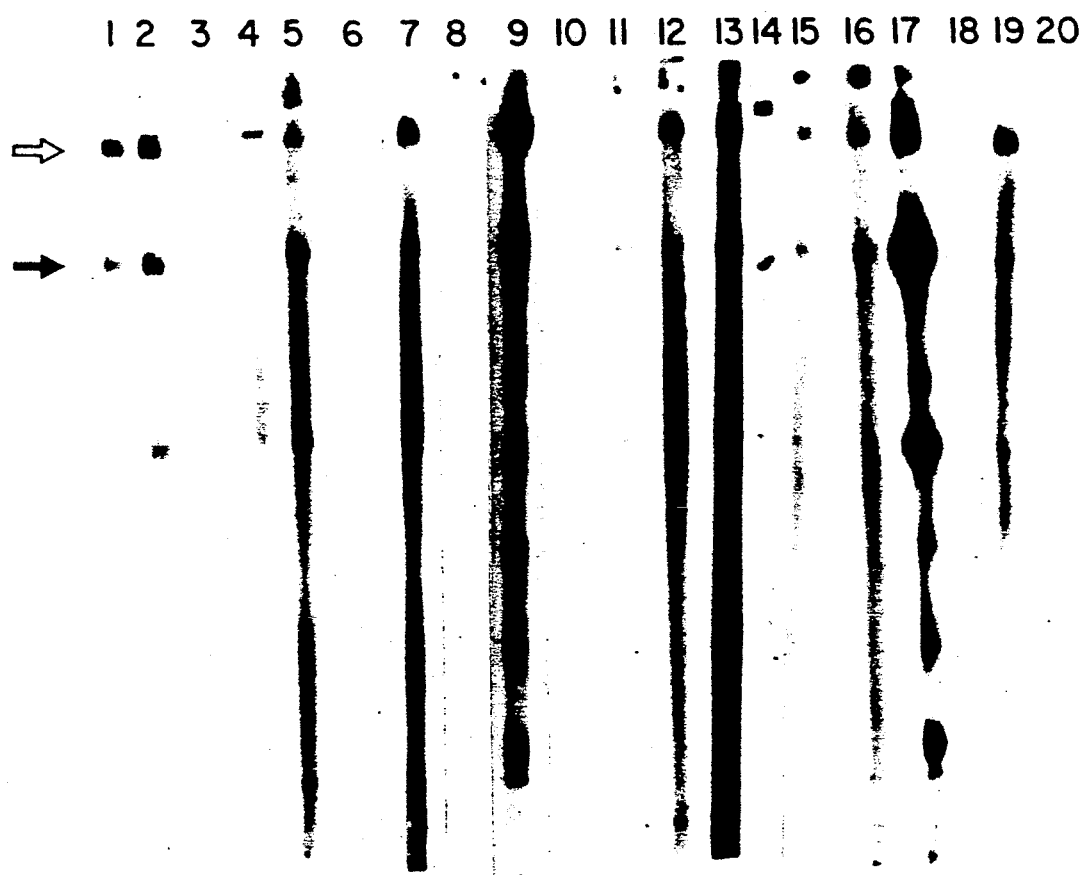
FIG. 3 is an autoradiograph generated out of an immunoblot analysis of monoclonal antibodies of the present invention.

The autoradiographic pattern generated by the nitro cellulose strips is shown in FIG. 3, and is read as follows: T3-1C9, T3-1C12, T3-1D8, T3-1E5, T3-1E7, T3-1E10, T3-2A9, T3-2B1, (lanes 1 through 8); T3-2D2, T3-2G4, T3-2H5, T3-2H6, T3-3F11, T3-3H1, T3-4A7, T3-4C11, T3-8B8, T3-8F5, T3-9E7 (lanes 10 through 20). In lane 9, incubation was with rabbit antiserum to crude *C. difficile* toxin. The control was hybridoma growth medium (not shown). The open arrow shows the position of toxin A. The closed arrow points to the major band of toxin B, which separates into a number of cytotoxic bands. From FIG. 3, it is apparent that the toxin B preparation contains a number of cytotoxic species, as reported by Rothman, 1984. A number of the monoclonal antibodies of the present invention were also shown by the abovedescribed blotting technique to recognize both toxin A and toxin B, confirming the RIA results. Four antibodies appeared to react more strongly in the blot with toxin A than with toxin B (see T3-1C9, T3-1E5, T3-2H5, T3-8F5); two (T3-1E7 and T3-4C11) appeared to react more strongly with toxin B than with toxin A. The remaining thirteen reacted equally with both toxins. There was no detection of either antigen in a control, in which medium used for growth of hybrids was substituted for monoclonal antibody.

To test for neutralization of cytotoxicity by monoclonal antibodies of the present invention, serial twofold dilutions of tissue culture supernatant fluids from each of the hybrid cell lines listed in Table 2 were mixed with an equal volume of complete minimal essential medium which contained 5 minimum cytotoxic doses of toxin A or toxin B. The toxin-antibody mixture, 100 μl per well, was incubated with HeLa cell monolayers over night at 35° C. The cells were fixed and stained and the dye absorbance at 595 nm was compared with controls, following the techniques of Rothman, 1984. None of the tested antibodies neutralized the cytotoxicity of either *C. difficile* toxin, as determined by the HeLa cell assay.

The monoclonal antibodies of the present invention, characterized by an affinity for both toxin A and toxin B of *C. difficile*, can be employed to advantage in various types of immunoassays for *C. difficile* in tissue and fecal samples. The antibodies can be used, for example, in "sandwich"-type assays, as described above, with horseradish peroxidase, alkaline phosphatase or some other well-known label material linked to a suitable antimouse antibody. See, e.g., VOLLER et al, THE ENZYME LINKED IMMUNOSORBENT ASSAY (ELISA) (Dynatech Laboratories 1979), the contents of which are hereby incorporated by reference. Particularly preferred is the modified double-antibody sandwich ELISA, wherein a plate provided with a layer comprised of antibody of the present invention is contacted first with a test sample (possibly toxin-containing) and thereafter with immunoglobulin solution containing a specific antibody (B) of a different species, such as goat or sheep. Enzyme-labelled anti-immunoglobulin which is reactive with antibody B, but not with the antibody of the present invention, is added to form the "double sandwich" (antibody/antigen/antibody B/anti-B globulin) for which the assay is named. When substrate for the enzyme is added, the resulting color change is proportional to the amount of *C. difficile* toxin (antigen) in the test sample.

The antibodies can also be used in RIA or other assay methods that are not solid-state assays, as well as ELISA's and dot-blot assays adapted from conventional protocols. By attaching a monoclonal antibody of the present invention to a substance which "tags" the antibody, one can also use the antibody as a diagnostic probe for *C. difficile* toxin in tissues of animals or humans.

Figure 1B:
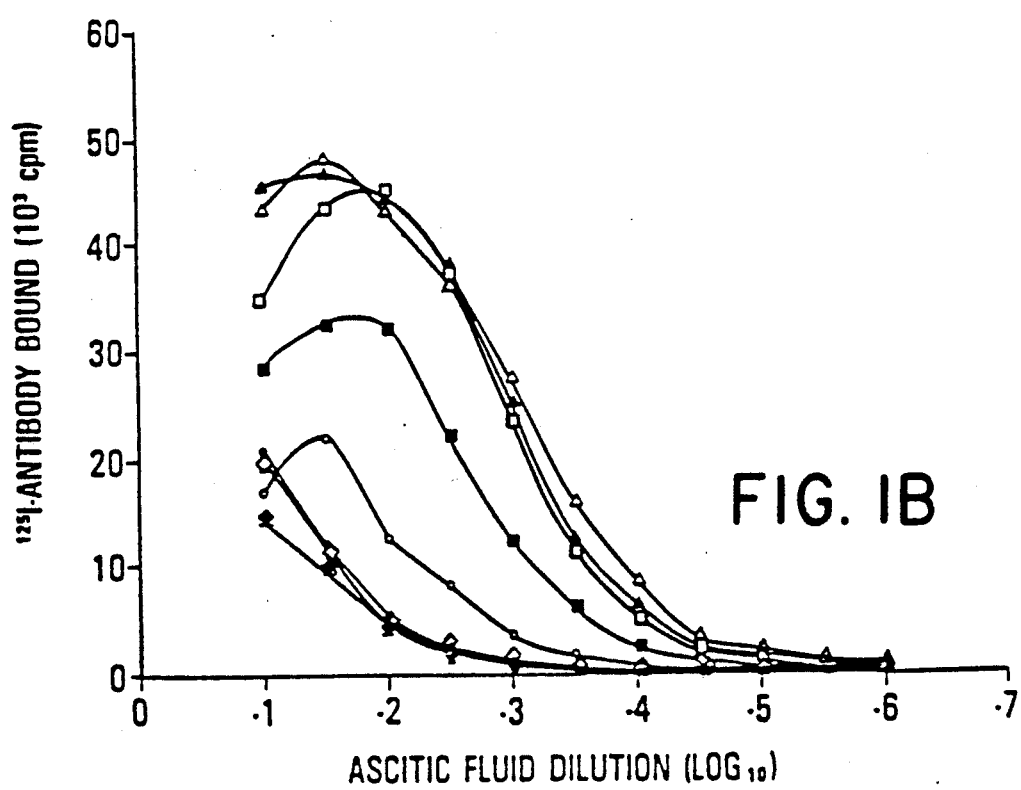
Figure 2A:
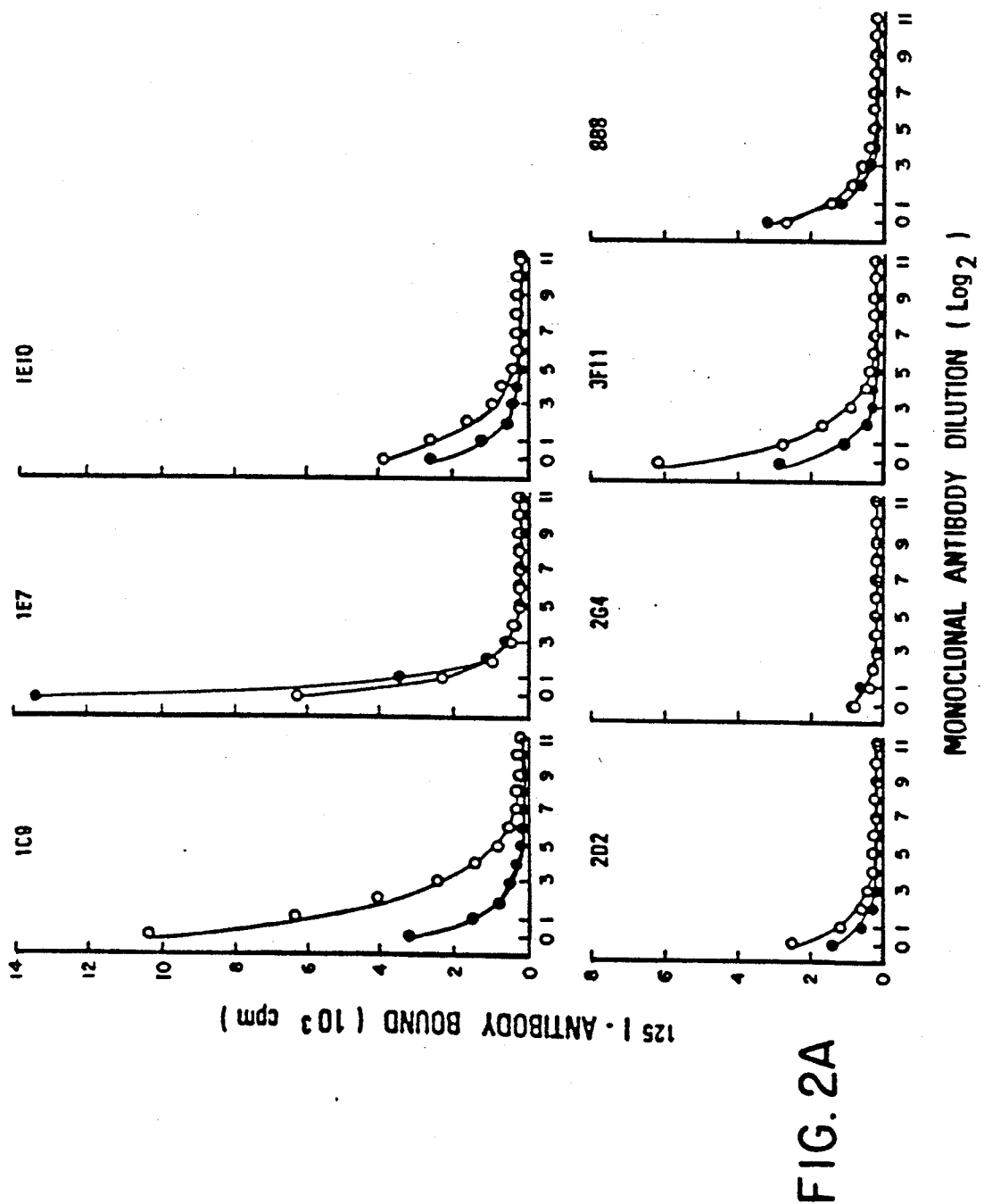
FIGS. 2A, 2B, 2C, and 2D are graphs showing the amounts of varying dilutions of monoclonal antibodies within the present invention that are bound by 380 ng of *C. difficile* toxin A and toxin B, respectively.
Figure 2B:
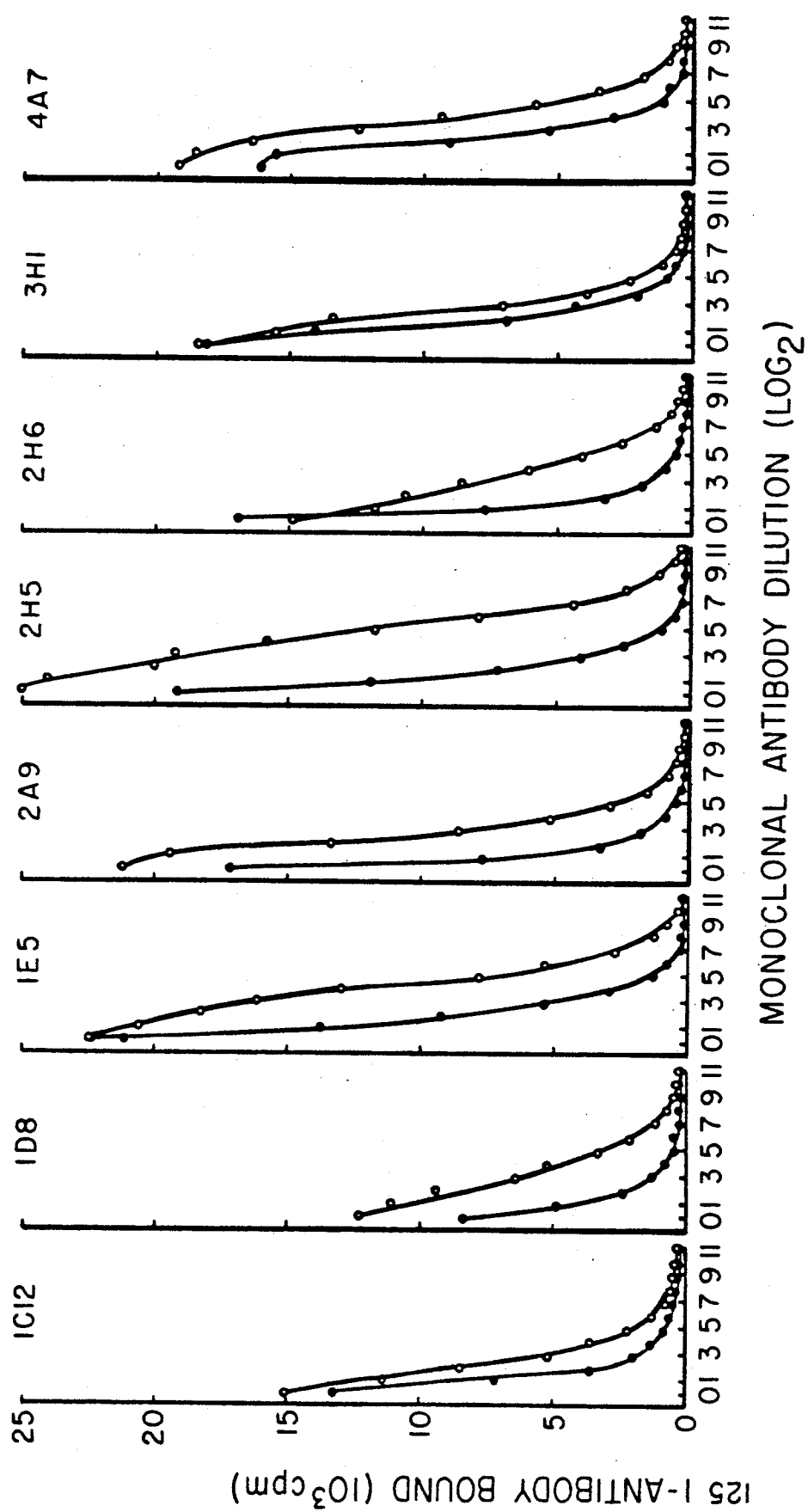
Figure 2C:
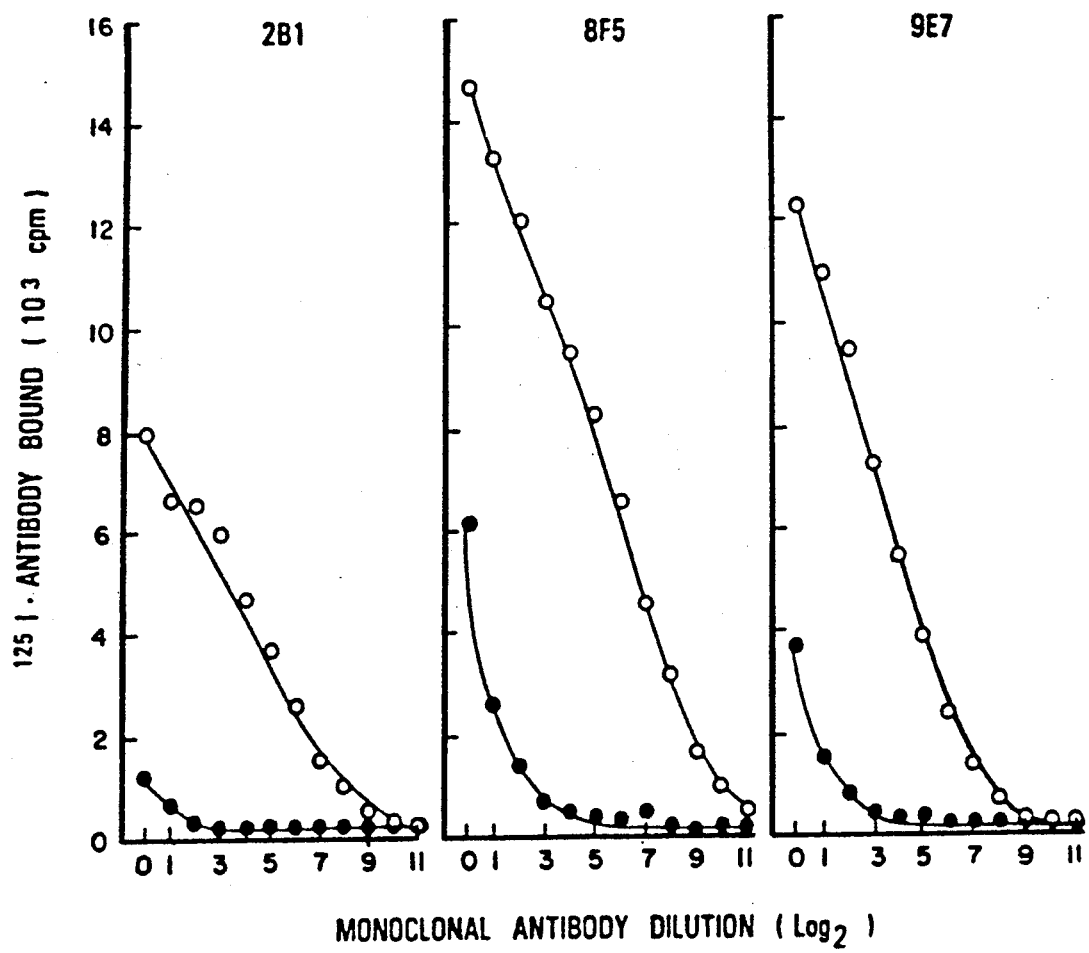
Figure 2D:
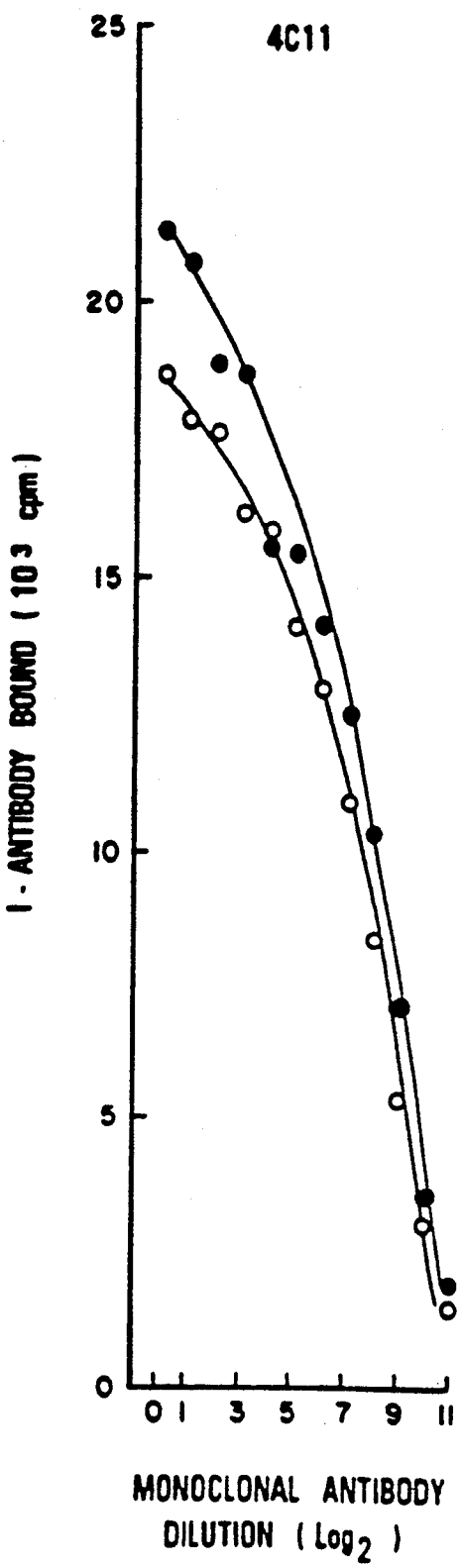

By the same token, the antibodies of the present invention can be used in an immunoassay for antibodies specific for both toxin A and toxin B. Adapting the protocol described above for identifying antibody-secreting cell lines prepared in accordance with the present invention, one can prepare assay plates coated with known amounts of toxin A and toxin B, as extrapolated from the concentration data in FIG. 1. One or more samples prepared from a biological material like blood serum, including human serum, to be tested for the presence of toxin A/toxin B-specific antibody are then prepared in a conventional manner and brought into contact, respectively, with the coated plates. Another set of plates are likewise contacted with samples containing a monoclonal antibody within the present invention. Both sets of plates are then contacted with a labeled detector substance, which can be protein A or an antibody that is broadly cross-reactive with immunoglobulin protein of the appropriate species, i.e., either the species of the test serum or mouse. (Protein A, found on the surface of certain strains of Staphylococcus aureus cells, binds to a specific portion of an antibody molecule. Labeled protein A, as well as labeled detecting antibody, can be prepared by known techniques, and is also commercially available.) The two sets of plates are then compared, with the detectable reactions on the plates containing the monoclonal antibody of the present invention serving as a standard for comparison with the plates containing the tested samples. If the test serum contains antibodies specific for toxin A and toxin B, a similar, detectable reaction should be observed.

What is claimed is:

1. A murine monoclonal antibody that immunologically binds both toxin A and toxin B of *Clostridium difficile*.

2. A continuous hybrid cell line that produces a murine monoclonal antibody which immunologically binds both toxin A and toxin B of *Clostridium difficile*.

3. A monoclonal antibody according to claim 1, wherein said antibody has an A/B reactivity ratio, as measured by radioimmunoassay, of between about 0.5 and about 6.9.

4. A monoclonal antibody according to claim 1, wherein said antibody is of the IgM isotype.

5. A monoclonal antibody according to claim 1, wherein said antibody is produced by a continuous hybrid cell line which is the product of a process comprising the step of fusing (i) a mouse spleen cell from a mouse immunized with a mixture comprising cytotoxically neutralized toxin A and toxin B and (ii) a mouse myeloma cell.

6. A monoclonal antibody according to claim 5, wherein said mouse myeloma cell is from a non-secretor cell line.

7. A monoclonal antibody according to claim 6, wherein said non-secretor cell line is the P3×63 Ag8.653 mouse myeloma line.

8. A monoclonal antibody according to claim 5, wherein said mouse is a BALB/c mouse.

9. A monoclonal antibody according to claim 5, wherein said mixture comprises toxin A and toxin B cytotoxically neutralized by incubation of each toxin with glutaraldehyde.

10. A monoclonal antibody according to claim 9, wherein each of said toxin A and said toxin B are incubated separately with glutaraldehyde.

11. A monoclonal antibody according to claim 5, wherein said cytotoxically neutralized toxin A and toxin B are the products, respectively, of a process comprising the steps of (a) subjecting a dialyzed culture filtrate of a *Clostridium difficile* strain to hydrophobic interaction chromatographic separation; (b) subjecting at least one cytotoxically active eluant of said hydrophobic interaction chromatographic separation to ion-exchange chromatography; and (c) concentrating at least one cytotoxically active eluant of step (b).

12. A monoclonal antibody according to claim 9, wherein step (c) comprises concentrating said cytotoxically active eluant of step (b) by dialysis or ultrafiltration.

13. A continuous hybrid cell line according to claim 2, wherein said cell line has the all the identifying characteristics of one selected from the group consisting of cell line T3-1C9, deposited under ATCC accession number HB9033; cell line T3-1C12, deposited under ATCC accession number HB9030; cell line T3-1D8, deposited under ATCC accession number HB9032; cell line T3-1E5, deposited under ATCC accession number HB9029; cell line T3-1E7, deposited under ATCC accession number HB9055; cell line T3-1E10, deposited under ATCC accession number HB9060; cell line T3-2A9, deposited under ATCC accession number HB9028; cell line T3-2B1, deposited under ATCC accession number HB9057; cell line T3-2D2, deposited under ATCC accession number HB9061; cell line T3-2G4, deposited under ATCC accession number HB9058; cell line T3-2H5, deposited under ATCC accession number HB9056; cell line T3-2H6, deposited under ATCC accession number HB9062; cell line T3-3F11, deposited under ATCC accession number HB9059; cell line T3-3H1, deposited under ATCC accession number HB9064; cell line T3-4A7, deposited under ATCC accession number HB9063; cell line T3-4C11, deposited under ATCC accession number HB9031; cell line T3-8B8, deposited under ATCC accession number HB9066; cell line T3-8F5, deposited under ATCC accession number HB9067; and cell line T3-9E7, deposited under ATCC accession number HB9065.

14. A monoclonal antibody according to claim 10, wherein step (a) comprises (i) adding ammonium sulfate to said culture filtrate and then (ii) applying said filtrate to a chromatography column which provides a distinctly nonpolar moiety in a matrix.

15. A monoclonal antibody according to claim 14, wherein said column is comprised of, a phenyl-substituted cross-linked agarose gel filtration medium.

16. A monoclonal antibody according to claim 11, wherein step (b) comprises applying said cytotoxically active eluant of said hydrophobic interaction chromatographic separation to column comprising a bead-formed, agarose gel anion exchange medium.

17. A monoclonal antibody according to claim 16, wherein said column is comprised of, a weak anion exchanger which preferentially binds biopolymers of greater than 10,000 molecular weight.

* * * * *